(12) United States Patent
Chen et al.

(10) Patent No.: US 6,552,007 B2
(45) Date of Patent: Apr. 22, 2003

(54) USE OF SOMATOSTATIN ANALOGS FOR THE DELIVERY OF ANTI-TUMOR DRUGS TO TUMOR CELLS

(75) Inventors: Shui-Tein Chen, Taipei (TW); Ying-Ta Wu, Tainan (TW); Chun-Ming Huang, Kaohsiung (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/734,298

(22) Filed: Dec. 11, 2000

(65) Prior Publication Data

US 2002/0094964 A1 Jul. 18, 2002

Related U.S. Application Data

(63) Continuation-in-part of application No. 09/482,451, filed on Jan. 13, 2000, now abandoned.

(51) Int. Cl.⁷ .................... A01N 57/00; A01N 61/00; A61K 38/00; C07K 14/00
(52) U.S. Cl. ................. 514/100; 514/1; 514/21; 514/16; 514/44; 530/300
(58) Field of Search ............. 530/300; 514/1, 514/21, 16, 44, 100

(56) References Cited

U.S. PATENT DOCUMENTS 5,359,030 A  * 10/1994 Ekwuribe ............... 530/303
5,843,903 A  * 12/1998 Schally et al. ............ 514/16
6,191,290 B1 *  2/2001 Safavy .................... 549/510

FOREIGN PATENT DOCUMENTS

WO         WO-9925729 A1 *  5/1999

OTHER PUBLICATIONS

Blume et al. Biochemica et Biophysica Acta vol. 1149, pp. 180–184, 1993.*

* cited by examiner

*Primary Examiner*—Jezia Riley
(74) *Attorney, Agent, or Firm*—Cohen, Pontani, Lieberman & Pavane

(57) ABSTRACT

A conjugate of somatostatin-spacer-drug and a method of making the same. The conjugate can be used to enhance an anti-cancer drug's specificity on the targeted tumor cells, thus increasing its therapeutic efficacy while reducing side-effects.

14 Claims, 5 Drawing Sheets

USE OF SOMATOSTATIN ANALOGS FOR THE DELIVERY OF ANTI-TUMOR DRUGS TO TUMOR CELLS

This is a continuation-in-part (CIP) of Application Ser. No. 09/482,451, filed on Jan. 13, 2000 now abandoned.

BACKGROUND OF THE INVENTION

1. Field of the Invention

The present invention relates to a novel anti-cancer drug delivery system, wherein a somatostatin analog is conjugated with an anticancer drug, such as paclitaxel, so that the anticancer drug can be delivered specifically to the targeted cancer cells.

2. Description of the Related Art

Most cytotoxic anticancer drugs suffer from a common problem, i.e. toxic side effects due to the lack of a selective drug delivery system. Using endocytotic ligands as carriers of the anticancer drugs to target these drugs to the cancer cells can avoid or reduce toxic side-effects and greatly improve the efficiency of these drugs' delivery.

Somatostatins function through cellular membrane receptors, known as somatostatin receptors (SSTR). These receptors are over expressed on the surfaces of certain tumor cells, such as carcinoid, islet cell of the pancreas, paragangliomas and small-cell carcinomas of lungs. Since somatostatin analogs possess such interesting properties, they may be used as a carrier system targeted to those malignant tumor cells such that the drugs can specifically act on those cells. It has been reported that somatostatin analogs including X-c[Cys-Phe-Trp-Lys-Thr-Cys]-X, X-c[-Cys-Tyr-D-Trp-Lys-Val-]-X, or X-c[Cys-Phe-D-Trp-Lys-Thr-Cys]-X are labeled with chromatic or radionuclide to visualize and monitor the tumors that express SSTRs. Somatostatin analogs are particularly preferred for these applications to the original somatostatins because such analogs are known to be smaller in size, higher in affinities to the somatostatin receptors, and more metabolism stable than the original somatostatins.

SUMMARY OF THE INVENTION

The present invention is directed to a combination of somatostatin analogs, such as octreotide, lanreotide, and vapreotide, and a cytotoxic drug, such as paclitaxel, through a covalent bond or a physical encapsulation. The inventive compound of the present invention has the following general structure:

X-spacer-NH-peptide wherein X is an anticancer drug, a lipid for making a liposome, or a monomer for forming a polymer matrix.

In general, this invention employs somatostatin analogs having sequence of X-c[Cys-Phe-Trp-Lys-Thr-Cys]-X, X-c[-Cys-Tyr-D-Trp-Lys-Val-]-X, or X-c[Cys-Phe-D-Trp-Lys-Thr-Cys]-X to provide a new system for delivering anticancer drugs to the cancer cells. The synthesis of somatostatin analogs is preferably performed on a solid-phase peptide synthesizer using Fmoc chemistry. The desired compound, such as anticancer drugs paclitaxel, doxorubicin or camptothecin or the like, that is intended to be delivered to the target cells, reacts with a spacer (preferably having a carboxyl terminal group) to form a covalent bond, resulting in a drug-spacer complex. Such complex is then coupled to the N-terminal of the somatostatin analog peptide on the resin to form the final product, namely, a drug-spacer-peptide complex, as shown in FIG. 1.

The present invention further provides a method of synthesizing a DOPE-PEG-spacer-somatostatin analog complex, which is useful for the preparation of a liposome drug delivery system, as shown in FIG. 1.

The various features of novelty that characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

Figure 1:
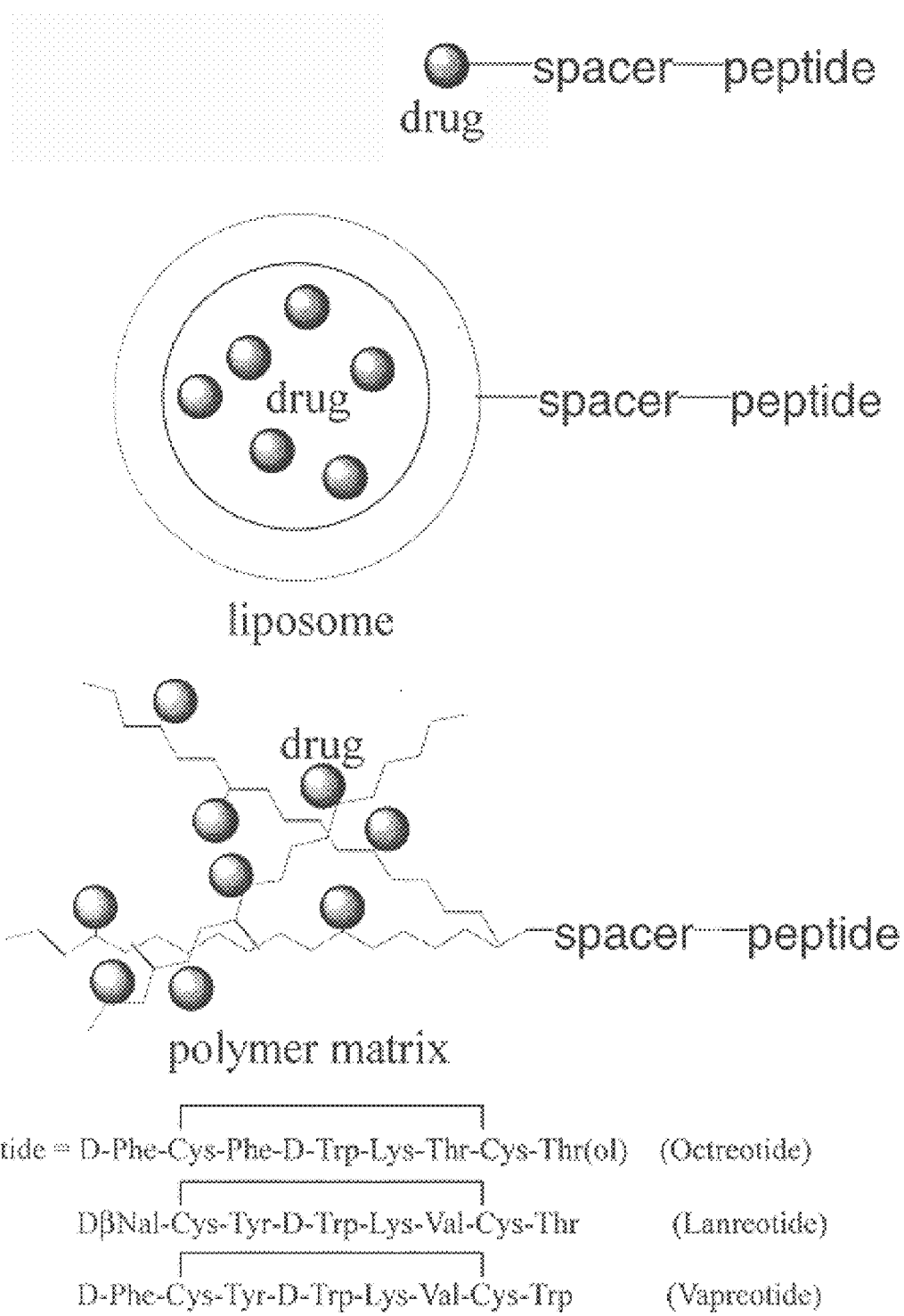
FIG. 1 shows general schemes of forming somatostatin analog conjugates and the sequences of the three preferred somatostatin analogs.

The abbreviations:

Fmoc: 9-fluorenylmethoxycarbonyl

Trt: triphenylmethyl

Thr-ol: threoninaol

Phe: phenylalanine

Cys: cysteine

Thr: threonine

Lys: lysine

Trp: tryptophan

DβNal: D-β-(2-naphthyl) alanine

TFA: trifluoroacetic acid

DMF: N,N-dimethylformamide

THF: tetrahydrofuran

HBTU: 2-(1 H-benzotriazol-1-yl)-1,1,3,3-tetramethyluronium hexafluorophosphate

DMAP: 4-dimethylaminopyridine

ACN: acetonitril

DCM: dichloromethan

TIS: Triisopropylsilane

PEG: polyethylene glycol

DOPE: dioleoyl phosphatidyl ethanolamine

MTT: 4,5-5-dimethyl thiazol-2,5-diphenyl-terasolium bromide

In a preferred embodiment, the formation of stable, covalently linked conjugates with fully retained biological activities of an anticancer drug is achieved by using a dicarboxylic acid spacer, such as glutaric acid. One carboxyl group of the spacer forms an ester bond with the 2'—OH group of anticancer drug paclitaxel or the —OH groups of other anticancer drugs and the other carboxyl group of the spacer forms a carboxamide bond with a well chosen free amino group of the peptide carrier, such as a somatostatin analog. While all somatostatin analogs that have free N-terminal amino groups may be chosen to conjugate with the anticancer drug or the like through the spacer, the particularly preferred peptide carriers are somatostatin analogs octreotide, lanreotide and vapreotide for their high affinities to human somatostatin receptors subtype 2 (for octreotide), 5 (for lanreotide) and 4 (for vapreotide). The sequences of the three preferred somatostatin analogs are shown as follows:

octreotide: D-Phe-c[Cys-Phe-D-Trp-Lys-Thr-Cys]-Thr(ol)

lanreotide: DβNal-c[Cys-Tyr-D-Trp-Lys-Val-Cys]-Thr-$NH_2$ vapreotide: D-Phe-c[Cys-Tyr-D-Trp-Lys-Val-Cys]-Trp-$NH_2$ The somatostatin analogs used for the purpose of the present invention may be synthesized using techniques known in the art, extracted from natural systems, or obtained from commercial sources (e.g. Peninsula, Neosystems, Sigma and BASF). A list of somatostatin analogs which may be used is described, for example, in "Somatostatin", Weil, Muller, and Thorner (eds.) (1992), the contents of which are incorporated herein by reference. Preferably, the somatostatin peptide is synthesized using conventional solid-phase synthetic techniques.

According to the present invention, in the preferred embodiment, the desired compound X is linked with one of the two carboxyl groups of a dicarboxylic acid spacer R while the somatostatin analog is linked with the other, which results in a general formula represented by:

X—O—R—NH—R' wherein —R— is —C(O)—$(CH_2)_n$—C(O)— and n=0–7, and R'— is a somatostatin peptide moiety.

It is contemplated that compounds having a general formula of $NH_2$—$(CH_2)_n$—COOH, SH—$(CH_2)_n$—COOH, $NH_2$—(PEG)—COOH, HOOC—(PEG)—COOH or HOOC—X-Maleimide may also be used as a spacer.

For the purpose of this invention, "spacer" is defined as a chemical compound which can form a covalent bond with an anti-cancer drug on one hand and another covalent bond with a somatostatin analog on the other hand, and "spacer component", "somatostatin component" and "drug component" refer to a spacer, a somatostatin analog and an anti-cancer drug in their integrated form in the drug-spacer-somatostatin conjugate, respectively. Preferably, a spacer used in practicing the present invention should have a suitable length and should not have a significant effect on either the drug's therapeutic property or the somatostatin analog's specific affinity to the receptors on the targeted tumor cells. Of course, the choice of a spacer in a specific practice depends on what type of anti-cancer drug it is to be conjugated to. For example, if the anti-cancer drug has a —OH group or a —$NH_2$ group for connecting a spacer, one should choose a spacer that has a —COOH group so that an ester bond can be formed between the —OH and —COOH groups or a peptide bond can be formed between the —$NH_2$ and —COOH; if the anti-cancer drug has a —COOH group for connecting a spacer, then one should choose a spacer that has a free —$NH_2$ group (in addition to the —$NH_2$ group which forms a peptide bond with the somatostatin analog) so that a peptide bond can be formed between the —COOH and —$NH_2$ groups; if the anti-cancer drug has a maleimide group, one should choose a spacer that has a free —SH group so that a covalent S-maleimide bond can be formed (and, vice versa, if the anti-cancer drug has a —SH group, the spacer should have a maleimide group). The conjugation between a maleimide group and a sulfhydryl group(—SH) has an additional advantage because the overall synthesis yield is increased as the conjugation can be conducted after the peptide cleavage and deprotection. This can prevent the anti-cancer drug from TFA treatment in the peptide cleavage and deprotection step. The following shows a number of specific spacer components listed as examples and not as a limitation to the present invention.

X1—CO—(—$CH_2CH_2$—)$_n$—$CH_2CH_2$—CO—NH-peptide;

X1—CO—(—$CH_2$—)$_n$—CO—NH-peptide;

X2—CO—(—$CH_2CH_2$—)$_n$—$CH_2CH_2$—CO—NH-peptide;

X2—CO—(—$CH_2$—)$_n$—CO—NH-peptide;

X3—NH—(—$CH_2CH_2O$—)$_n$—$CH_2CH_2$—CO—NH-peptide;

X3—NH—(—$CH_2$—)$_n$—CO—NH-peptide;

X4—S—(—$CH_2CH_2O$—)$_n$—$CH_2CH_2$—CO—NH-peptide;

X4—S—(—$CH_2$—)$_n$—CO—NH-peptide;

X5-maleimide-(—$CH_2CH_2O$—)$_n$—$CH_2CH_2$—CO—NH-peptide;

X5-maleimide-(—$CH_2$—)$_n$—CO—NH-peptide;

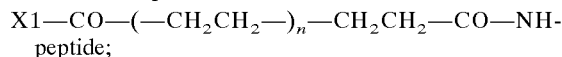
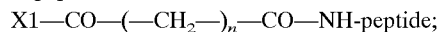
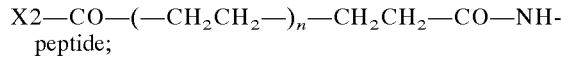
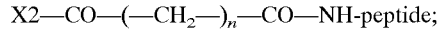
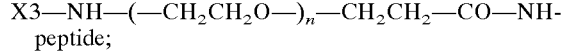
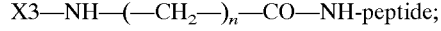
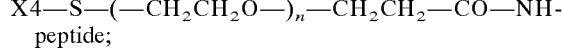
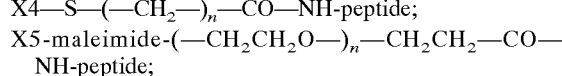
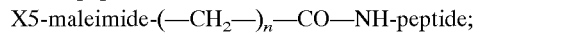
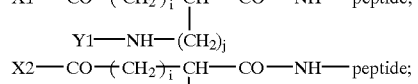
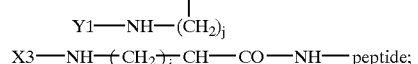
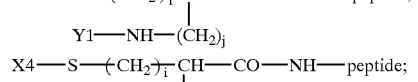
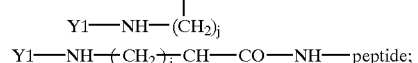
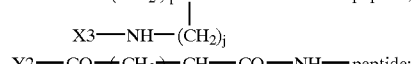
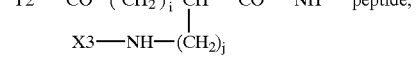
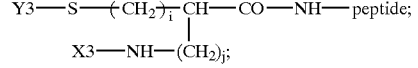

where n=1–7; i=1–4; j=1–2; X1 is a drug component formed from an anti-cancer drug that has a —OH group for forming a covalent bond; X2 is a drug component formed from an anti-cancer drug that has a —$NH_2$ group for forming a covalent bond; X3 is a drug component formed from an anti-cancer drug that has a —COOH group for forming a covalent bond; X4 is a drug component formed from an anti-cancer drug that has a maleimide group for forming a covalent bond; X5 is a drug component formed from an anti-cancer drug that has a —SH group for forming a covalent bond; and peptide is a somatostatin component; Y1=$CH_3$—O—(—$CH_2CH_2O$—)$_m$—$CH_2CH_2$—CO— where m=45–225 or Y1=Sugar-CO— where Sugar is glucose, sialic acid or one of their derivatives; Y2=CH$_3$—O—(—CH$_2$CH$_2$O—)$_m$—CH$_2$CH$_2$—NH—0 where m=45–225; Y3=CH$_3$—O—(—CH$_2$CH$_2$O—)$_m$—CH$_2$CH$_2$-maleimide where m=45—225.

Because some anti-cancer drugs, such as taxol, have poor water solubility, a conjugated drug-spacer-somatostatin complex can have a free —NH$_2$ group for further connection to a component which can improve the drug's water solubility. For instance, the —NH$_2$ can be connected to a PEG, sugar or biotin group as in the following example:

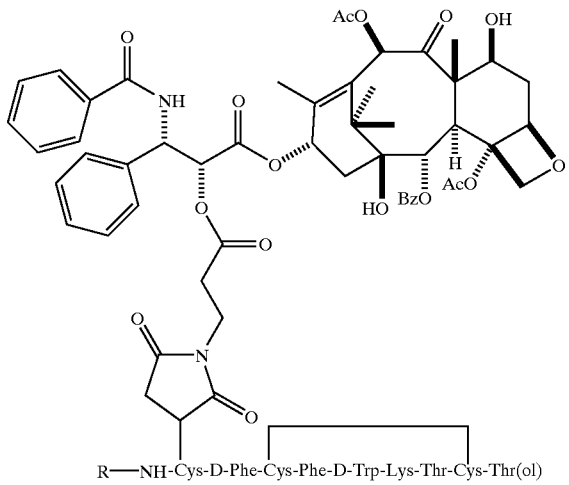

R—NH-Cys-D-Phe-Cys-Phe-D-Trp-Lys-Thr-Cys-Thr(ol)

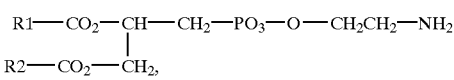

where n=1–7; i=1–4; j=1–2; Y1=CH$_3$—O—(—CH$_2$CH$_2$O—)$_m$—CH$_2$CH$_2$—CO— where m=45–225 or Y1=Sugar-CO— where Sugar is glucose, sialic acid or one of their derivatives; X2 is phosphatidylethanoamine (PE) having the formula of $$R1—CO_2—CH—CH_2—PO_3—O—CH_2CH_2—NH_2$$
$$R2—CO_2—CH_2,$$

where R1 and R2 ae alkyls.

Examples of phosphatidylethanoamie are dioleoyl PE (DOPE) and distearoyl PE (DSPE). Their structures are shown below:

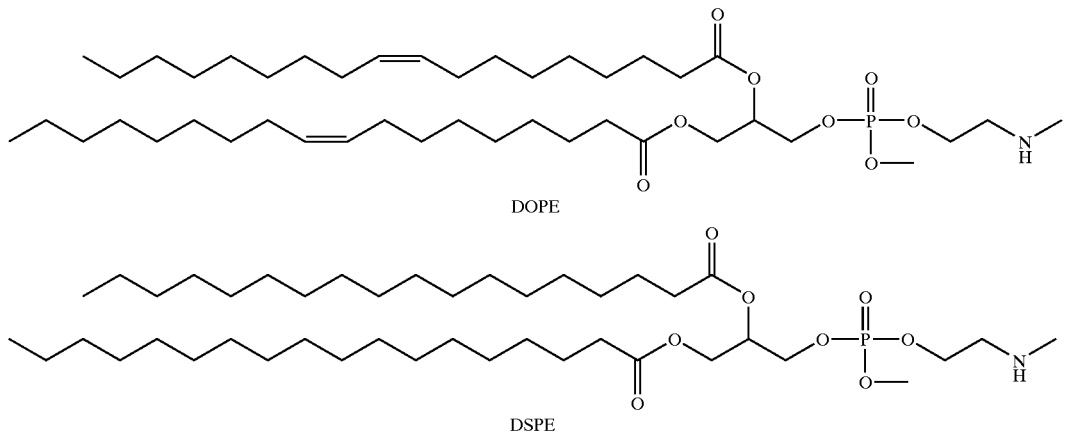

DOPE

DSPE wherein R is a H, biotin, sugar or PEG group.

It is further contemplated that, to practice the present invention, somatostatin analog does not have to be conjugated directly to an anti-cancer drug X. Rather, the somatostatin analog-drug connection can be achieved indirectly. One example of such indirect connection is through liposomes, where somatostatin analog is covalently connected to a compound which then forms liposomes, where one or more anti-cancer drugs can be disposed (see FIG. 1). The drug in the liposomes will be released once the conjugated somatostatin analog brings the liposomes to the targeted tumor cells. The art of using liposomes as a drug delivery vehicle has been known and detailed discussion thereof is believed unnecessary. The following are some examples where somatostatin is conjugated with a liposome-forming compound, such as phosphatidylethanoamine (PE).

Again, the above listing are examples and not a limitation to the present invention.

In addition to indirect linking through liposomes, another method of indirect connection is through formation of a polymer matrix, see FIG. 1, where a somatostatin analog is covalently bound to monomers, such as poly(ethylene glycol) monomethacrylate (Shearwater Polymers, Huntsville, Ala.), which then cross linked or grafted by a free radical suspension polymerization to form a polymer matrix with one or more anti-cancer drugs disposed therein (either by physical trapping or chemical bonding). When the somatostatin analog brings the polymer matrix to the targeted tumor cells, the drugs can be released. The art of using a polymer matrix as a drug delivery has been known and detailed discussion thereof is believed unnecessary.

The anti-cancer drug used in the preferred embodiment, paclitaxel, may be obtained from a commercial source (e.g.

Bristol-Myers-Squibb), purified from a natural source or chemically synthesized using techniques known in the art. Both PEG and DOPE are generally available.

Once the drug-somatostatin conjugates are formed through the spacer, their biological activities can be tested using cell culture techniques.

Figure 2:
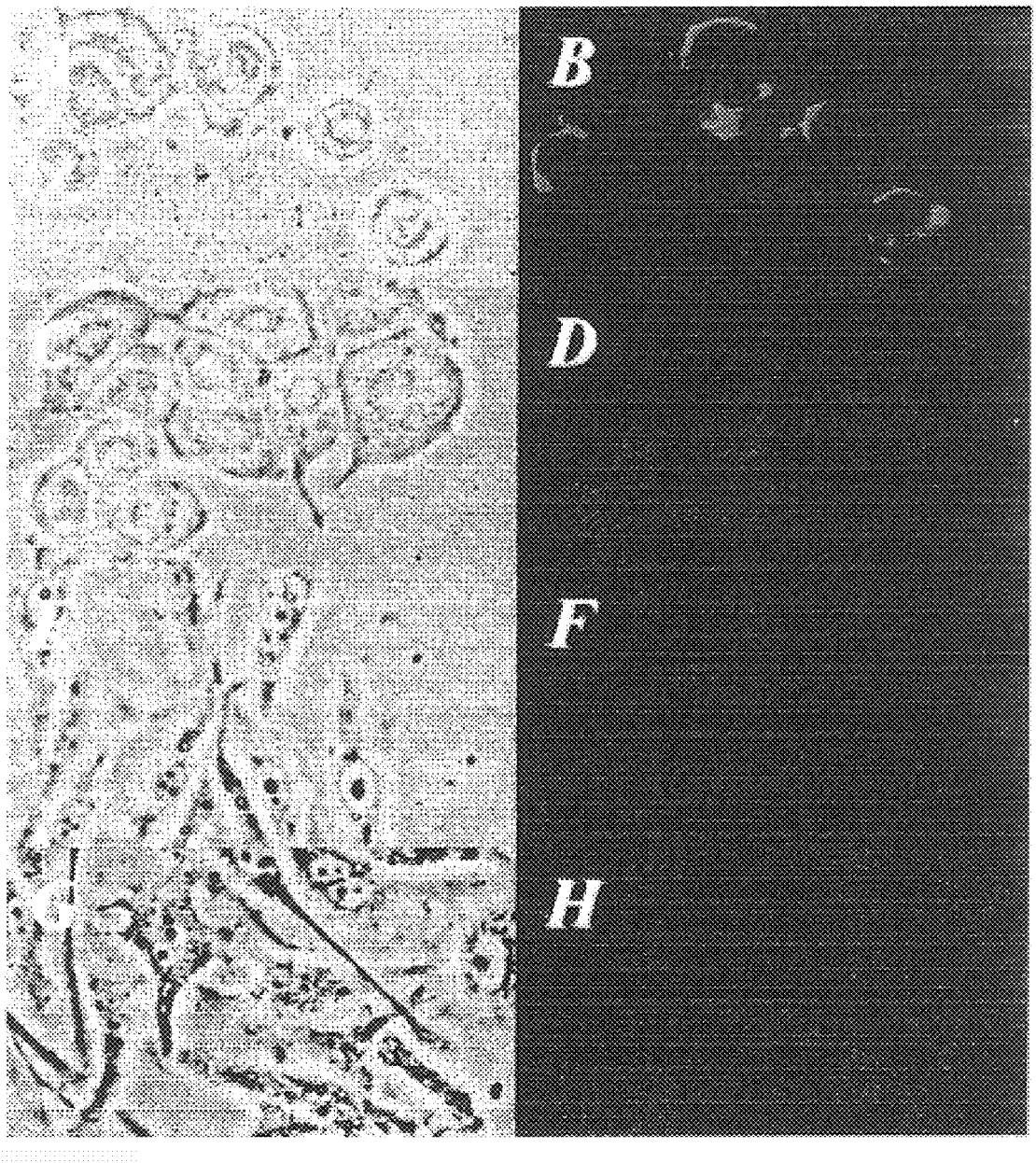
FIG. 2 depicts fluorescence micrographs of MCF-7 and CHO cells after incubation with fluorescin-octreotide at 4° C. for 30 min. The labeling is confined to the MCF-7 cell surface (B) and disappears when the MCF-7 cells were incubated in the presence of an excessive amount (1,000 fold) of nonfluorescent octreotide (D). No labeling can be seen among the CHO cells (F), even these cells were incubated with a higher concentration (500 μg/ml) of fluorescin-octreotide (H). Cell morphology was shown at A, C, E, and G. Bar=20 μm.

Referring now to FIG. 2, specific binding of octreotide to the MCF-7 cells but not the CHO cells is shown in fluorescence micrographs. panels A and C, and E and G show the morphology of the MCF-7 cells and CHO cells. Panels B, D, F and H which correspond to panels A, C, E and G, respectively, show the fluorescence labeled octreotide binding to the MCF-7 cells and the CHO. The MCF-7 cells and CHO cells are incubated with 100 μg of fluorescein labeled octerotide in 1 ml of a buffer for 30 minutes at 4 ° C., after which the cells are washed with PBS, fixed with 4% paraformaldehye and subject to fluorescence microscopy. As shown in panels B and F, the octreotide binds to the MCF-7 cells (B) but not to the CHO cells (F). The octreotide binding to the MCF-7 cells disappears in the presence of an excessive non-labeled octreotide to compete with the labeled octreotide (panel D). The octreotide does not bind to the CHO cells even when the CHO cells are given a higher concentration of labeled octreotide (panel H).

Figure 3:
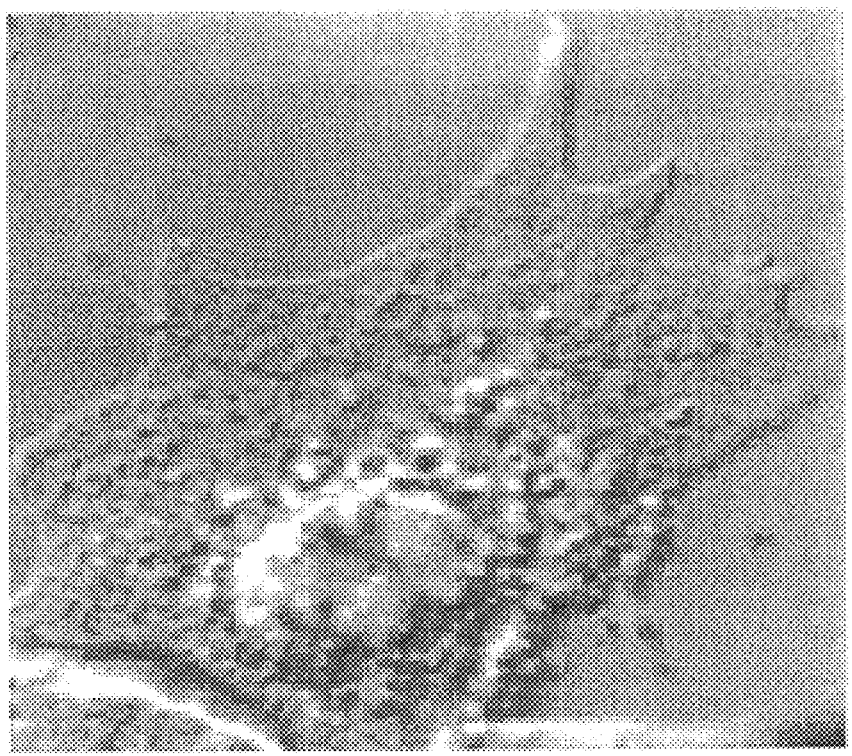
FIG. 3 shows the internalization of fluorescin-octreotide by the MCF-7 cells. Bar=5 μm.
Figure 3:
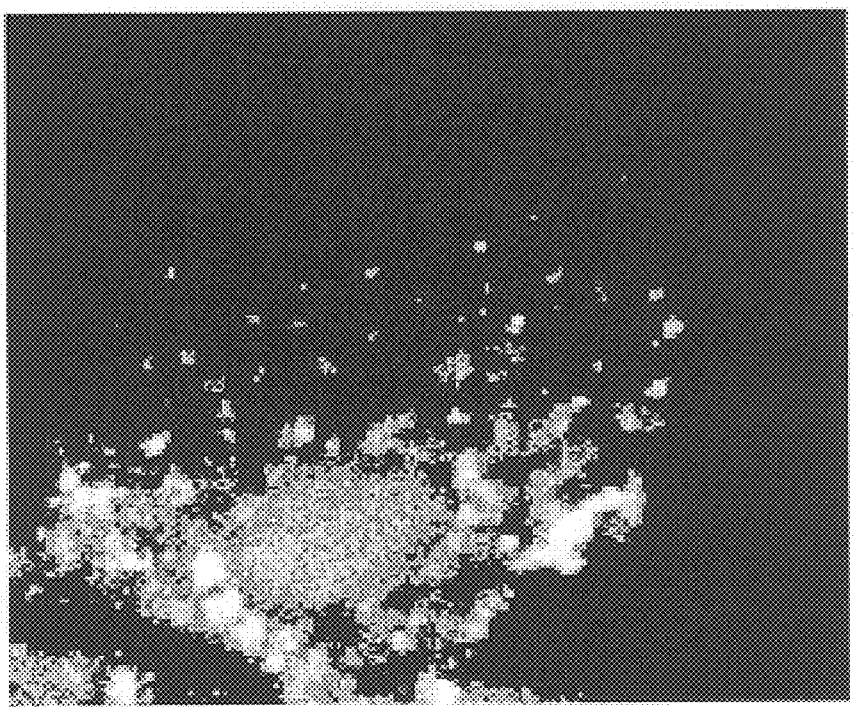

FIG. 3 shows that the labeled octreotide bound to the MCF-7 cells was internalized into the MCF-7 cytosol via somatosatin receptor-mediated endocytosis after one hour incubation with 100 μg/ml of the labeled octreotide at 37° C.

Figure 4:
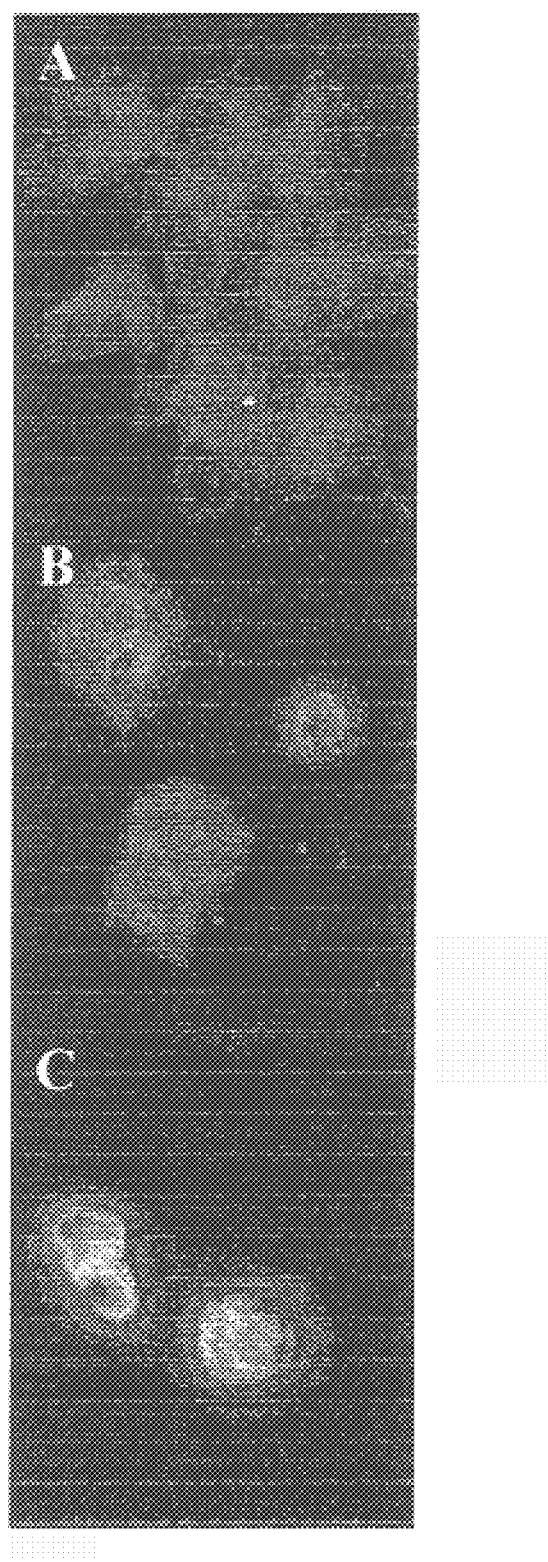
FIG. 4 shows that the octreotide-conjugated taxol virtually retains the cellular functions of taxol.

Referring now to FIG. 4, the octreotide conjugated paclitaxel exhibits the same anti- tumor activity through disrupting microtubule formation of the cells as the non-conjugated paclitaxel. Panel A shows distribution of tubulin in the MCF-7 cells, where the cells were incubated in the absence (A1) or presence (A2) of $10^{-6}$ M paclitaxel, or in the presence of octreotide-conjugated paclitaxel (A3). Bar=20 μm. B and C: Chromatin condensation in apoptotic cells, where the ultrastructure of apoptotic MCF-7 cells were observed by transmission electron micrograph (B, X 7,500, bar=500 nm) or the Nuclei were stained with Hoechst 33258 and fluorescence photomicrographs (C, bar=10 μm); the MCF-7 cells being treated without (B1 and C1) or with (B2 and C2) $10^{-6}$ M paclitaxel or with octreotide-conjugated paclitaxel (B3 and C3) for 1 day.

Figure 5:
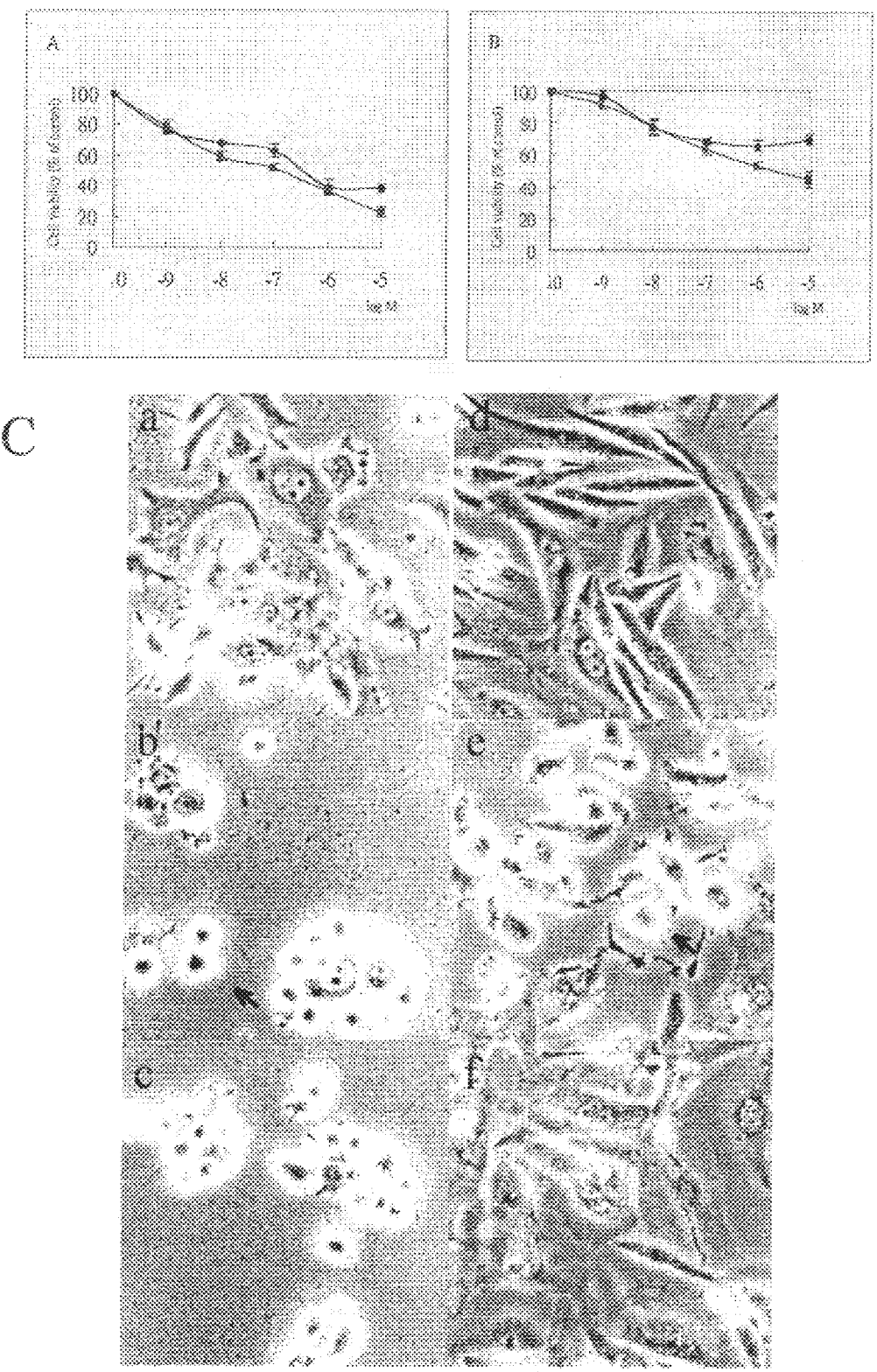
FIG. 5 shows that the octreotide-conjugated paclitaxel is specific to MCF-7 cells.

Cell-specificity of the octreotide-conjugated paclitaxel is shown in FIG. 5, where panels A1 and B1 are the untreated MCF-7 cells and CHO cells, respectively; panels A2 and B2 are MCF-7 cells and CHO cells, respectively, treated with paclitaxel ($10^{-5}$ M) for 1 day; and panels A3 and B3 show the MCF-7 cells and CHO cells, respectively, treated with the octreotide conjugated paclitaxel ($10^{-5}$ M) for 1 day. Unlike the free paclitaxel, which causes death of both MCF-7 cells and CHO cells, the octreotide conjugated paclitaxel induces only the death of the MCF-7 cells but not of the CHO cells as shown in panels A3 and B3. Cell death is indicated by arrows, bar=20 =m.

The novel somatostatin-conjugated compounds of the present invention may be used for treating a cancer patient by administering the anticancer compounds to the cancer patient in a composition comprising the above described compounds and a pharmaceutically acceptable carrier.

The practice of the invention is further illustrated by the following examples, but the illustration does not limit the scope of this application.

EXAMPLE 1

Synthesis of Paclitaxel-Glutary 1-Octreotide

Paclitaxel (0.43 g, 0.5 mmol) and glutaric anhydride (0.68 g, 6 mmol) were dissolved in 5 ml of pyridine and stirred at room temperature for 3 hours. In the end of reaction, the solution was evaporated to dryness in vacuo. The residues were treated with 20 ml water with stirring for 20 min and filtered. The precipitates were redissolved in acetone and water was added to produce fine crystals of paclitaxel-glutarate (0.42 g, 86% yields). The analytic result gave $[M+H]^+=968$ Da by ESMs. The paclitaxel-glutarate complex has the following structure:

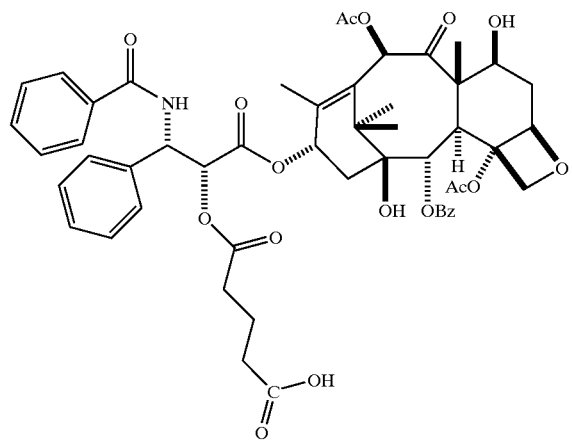

The sequence of octreotide was synthesized using solid-phase Fmoc chemistry, which has an assembly chain of $NH_2$-D-Phe-Cys(Trt)-Phe-D-Trp-Lys(Mtt)-Thr-Cys(Trt)-Thr-ol-Acetal-Siber Amide Resin (0.1 mmol). Four molar equivalent of paclitaxel-glutarate activated by HBTU was added as the ninth amino acid derivative to couple octreotide. The final of reaction was monitored using ninhydrine test that measures the diminished free amino group at N-terminal.

Cleavage of the peptide conjugate from amide resin was performed using 1% TFA/5% TIS/DCM. The cleaved compounds were neutralized by 15% pyridine/methanol and diluted with pH 7.5 buffer to complete disulfide-formation and lyophilized to 135 mg of the crude product. Further purification may be performed by HPLC with a preparative column and $ACN/H_2O$ eluent system. The analytic result gave $|M+H|^+=1969$ Da by ESMs and following structure:

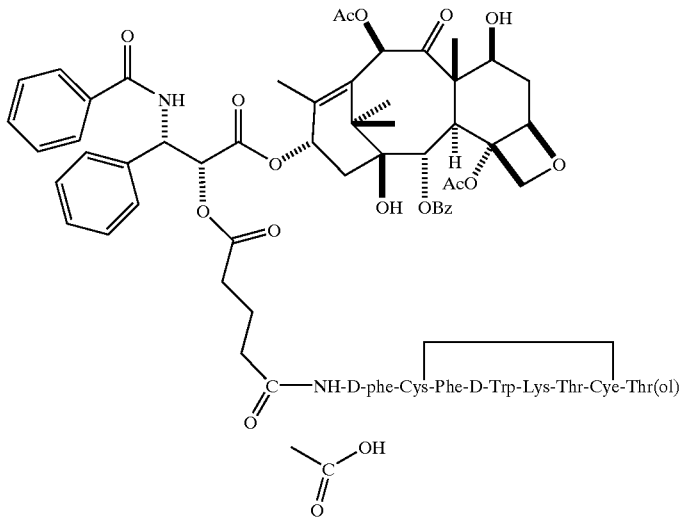

EXAMPLE 2

Synthesis of Fluorescein-Octreotide

Four equivalent molar of 5-Carboxy-fluorescein (0.4 mmole) were coupled to the assembly chain of $NH_2$-β-Ala-D-Phe-Cys(Trt)-Phe-D-Trp-Lys(Mtt)-Thr-Cys(Trt)-Thr-ol-Acetal-Siber Amide Resin (0.1 mmol) as an amino acid derivatives. Cleavage of the peptide conjugate from amide resin was performed using 95% TFA/5% TIS. After evaporation of TFA under vacuum, the peptide was precipitated with addition of ice cold dry ether. The precipitates were filtered, washed with cold ether on a sintered glass funnel, and extracted with 20% acetic acid solution. The peptide product was diluted to about 1 mM with 5% ammonium acetate solution and the pH was adjusted to 7.5 with ammonium hydroxide (25%) to accomplish disulfide-formation. The sample was then lyophilized to powder. The analytic result gave $[M+H]^+$ m/z 1448 Da by ESMs.

EXAMPLE 3

Synthesis of DOPE-PEG-Octreotide

PEG (1 g, 0.5 mmole) and succinic anhydride (0.1 g, 1 mmole) were dissolved in THF with addition of DMAP. The solution was stirred at 50° C. with reflux for six hours. In the end of reaction, the solution was evaporated in vacuo to produce di-succinyl-PEG, which was purified by flash chromatography of the residue over silica gel. Four equivalent molar of di-succinyl-PEG(0.4 mmole) and four equivalent of DOPE (0.4 mmole) were coupled to the assembly chain of $NH_2$-D-Phe-Cys(Trt)-Phe-D-Trp-Lys(Mtt)-Thr-Cys(Trt)-Thr-ol-Acetal-Siber Amide Resin (0.1 mmol) sequentially as the ninth and the tenth of amino acid derivatives. Cleavage of the peptide conjugate from amide resin was performed using 1% TFA/5% TIS/DCM. The cleaved compounds were neutralized with 15% pyridine/methanol, diluted with a buffer of pH 7.5 to complete disulfide-formation, and lyophilized to crude product having the structure below. This product was used in the liposome preparation.

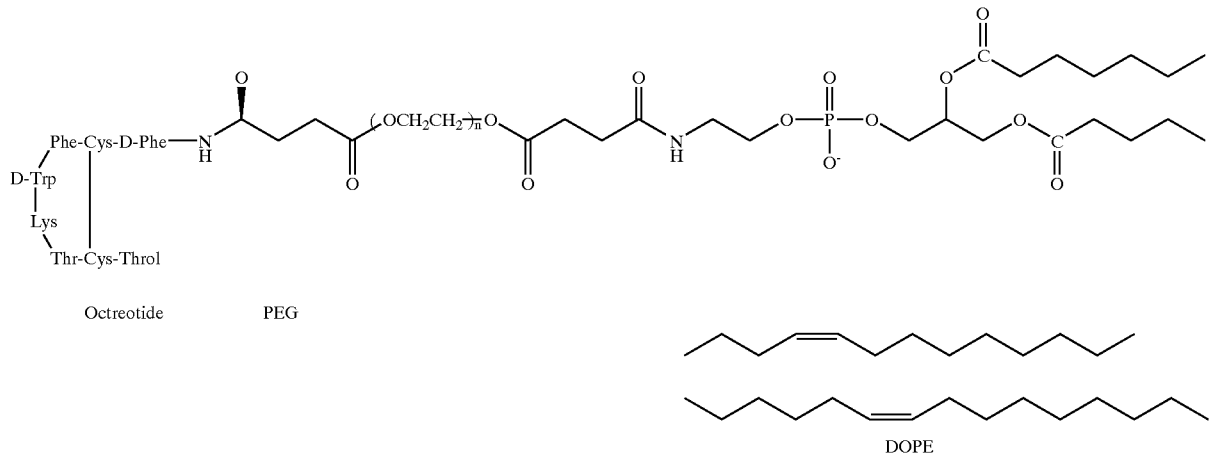

EXAMPLE 4

Liposome Preparation

Liposome was prepared by lipid/detergent mixed micelles followed by controlled dialysis. A solution of DSPC/cholestrol/DOPE-PEG-octreotide (molar ratio 10:1:1) in 10 ml chloroform/ethanol (2:1 v/v) was mixed with sodium cholate (lipid/cholate molar ratio 0.6) and evaporated to dryness under reduced pressure in a round-bottom flask at 55° C. The remaining thin film was dispersed in 5 ml 10 mM phosphate buffer pH 7.4 which was adjusted to 0.16 ionic strength. The mixed micelles were spontaneously formed. After short equilibration, the mixed micellar solution was dialyzed at 60° C. for 24 hours with the MINI-LIPOPREP$^R$ (Sialomed, Inc., USA) using cellulose disk membranes having a 10,000 molecular weight cut off. The liposome so prepared was directly used for assay.

The invention is not limited by the embodiments described above which are presented as examples only but can be modified in various ways within the scope of protection defined by the appended patent claims.

SEQUENCE LISTING

Although this application contains three amino acid sequences, it is believed that no separate sequence listing is required because those sequences are branched and contain D amino acid residues. 37 CFR 1.821; MPEP 2421.02.

We claim:

1. A compound comprising a somatostatin analog moiety, a spacer moiety and an anti-cancer drug moiety, said spacer moiety is selected from the group consisting of —CO—(—$CH_2CH_2O$—)$_n$—$CH_2CH_2$—CO—;
—CO—(—$CH_2CH_2O$—)$_n$—$CH_2CH_2$—CO—;
—NH—(—$CH_2CH_2O$—)$_n$—$CH_2CH_2$—CO—;
—NH—(—$CH_2$—)$_n$—CO—;
—S—(—$CH_2CH_2O$—)$_n$—$CH_2CH_2$—CO—;
—S—(—$CH_2$—)$_n$—CO—NH-peptide;
—(—$CH_2CH_2O$—)$_n$—$CH_2CH_2$—CO—; and
-maleimide-(—$CH_2$—)$_n$—CO—;

where n=1–7.

2. The compound of claim 1, wherein said spacer is covalently bound to said anti-cancer drug moiety and said somatostatin analog moiety.

3. The compound of claim 2, wherein said somatostatin analog moiety is selected from octreotide, lanreotide, and vapreotide.

4. The compound of claim 1, having a structural formula selected from the group consisting of:

X1—CO—(—$CH_2CH_2O$—)$_n$—$_{CH2}CH_2$—CO—NH—R;
X2—CO—(—$CH_2CH_2O$—)$_n$—$CH_2CH_2$—CO—NH—R;
X3—NH—(—$CH_2CH_2O$—)$_n$—$CH_2CH_2$—CO—NH—R;
X3—NH—(—$CH_2$—)$_n$—CO—NH—R;
X4—S—(—$CH_2CH_2O$—)$_n$—$CH_2CH_2$—CO—NH—R;
X4—S—(—$CH_2$—)$_n$—CO—NH—R;
X5-maleimide-(—$CH_2CH_2O$—)$_n$—$CH_2CH_2$—CO—NH—R; and
X5-maleimide-(—$CH_2$—)$_n$—CO—NH—R;

where r=1–7; X1 is an anti-cancer drug moiety that has a —OH group for connecting to said spacer; X2 is an anti-cancer drug moiety that has a —$NH_2$ group for connecting to said spacer; X3 is an anti-cancer drug moiety that has a —COOH group for connecting to said spacer; X4 is an anti-cancer drug moiety that has a maleimide group for connecting to said spacer; X5 is an anti-cancer drug moiety that has a —SH group for connecting to said spacer component; and R represents said somatostatin analog moiety.

5. A compound comprising a somatostatin analog moiety, a spacer moiety and an anti-cancer drug moiety, said compound having a structural formula selected from the group consisting of:

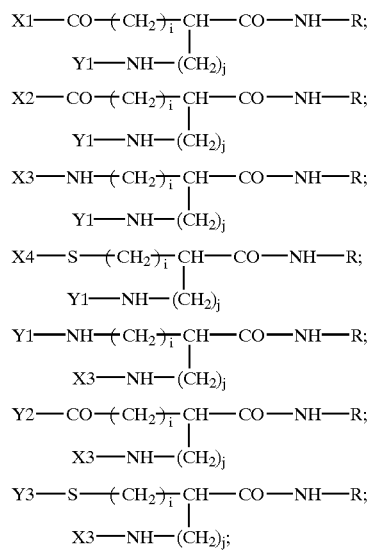

wherein i=1–4; j=1–2; X1 is an anti-cancer drug moiety that has a —OH group for connecting to said spacer moiety; X2 is an anti-cancer drug moiety that has a —$NH_2$ group for connecting to said spacer moiety; X3 is an anti-cancer drug moiety that has a —COOH group for connecting to said spacer moiety; X4 is an anti-cancer drug moiety that has a maleimide group for connecting to said spacer moiety; X5 is an anti-cancer drug moiety that has a —SH group for connecting to said spacer moiety; and R is said somatostatin analog moiety; Y1=$CH_3$—O—(—$CH_2CH_2O$—)m—$CH_2CH_2$—CO— where m=45–225 or Y1=Sugar-CO— where Sugar is glucose, sialic acid or their analogues; Y2=$CH_3$—O—(—$CH_2CH_2O$—) m—$CH_2CH_2$—NH— where m=45–225; Y3=$CH_3$—O—(—$CH_2CH_2O$)$_m$—$CH_2CH_2$-maleimide where m=45–225.

6. A compound having the following structure:

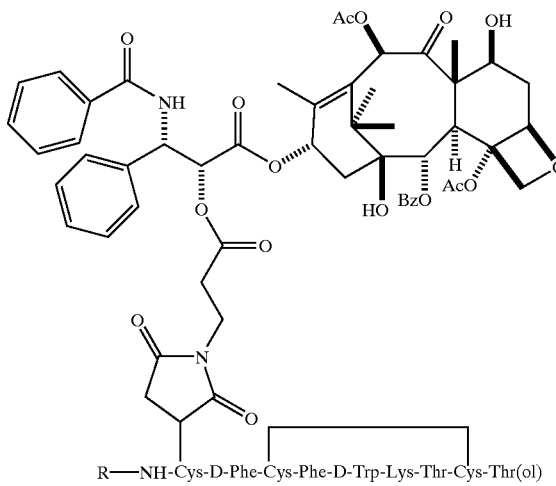

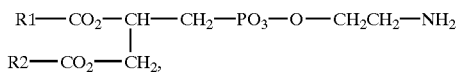

wherein R is a H, biotin, sugar or PEG group.

7. A compound having a structural formula selected from the group consisting of:

X2—CO—(—CH$_2$CH$_2$O—)$_n$—CH$_2$CH$_2$—CO—NH—R;

X2—CO—(—CH$_2$—)$_n$—CO—NH—R;

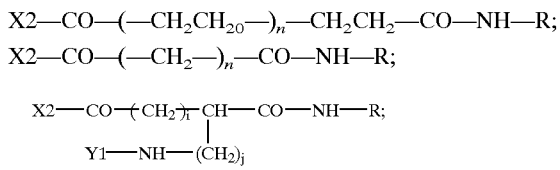

wherein n=1–7; i=1–4; j=1–2; R is a somatostatin analog moiety; Y1=CH$_3$—O—(—CH$_2$CH$_2$O—) m—CH$_2$CH$_2$—CO— where m=45–225 or Y1=Sugar-CO— where Sugar is glucose, sialic acid or their analogues X2 is a phosphatidylethanoamine having the structural formula of:

R1—CO$_2$—CH—CH$_2$—PO$_3$—O—CH$_2$CH$_2$—NH$_2$
R2—CO$_2$—CH$_2$, where R1 and R2 are alkyls.

8. The compound of claim 7, wherein said phosphatidylethanoamine is dioleoyl PE or Distearoyl PE.

9. A compound having the following structure:

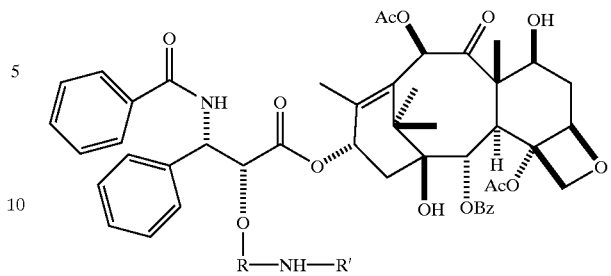

wherein R represent a spacer component and R' represents a somatostatin component.

10. The compound of claim 9, wherein said somatostatin component is selected from the group consisting of octreotide, lanreotide, and vapreotide.

11. The compound of claim 9, wherein said spacer component R is a dicarboxylic acid.

12. The compound of claim 11, wherein said dicarboxylic acid has a structure of

—CO—(—CH$_2$—)$_n$—CO—; or

—CO—(—CH$_2$CH$_2$O—)$_n$—CH$_2$CH$_2$—CO—, wherein n=1–7.

13. The compound of claim 12, wherein said somatostatin component is selected from the group consisting of octreotide, lanreotide, and vapreotide.

14. The compound of claim 13 having the following structure

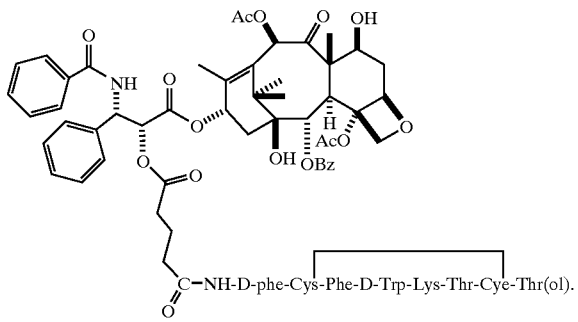

* * * * *